US012329959B2

(12) United States Patent
Almedhychy et al.

(10) Patent No.: US 12,329,959 B2
(45) Date of Patent: Jun. 17, 2025

(54) SYSTEMS AND METHODS FOR DETERMINING POSITIONING OF INTRACARDIAC DEVICES

(71) Applicant: ABIOMED, Inc., Danvers, MA (US)

(72) Inventors: Ali Hassan Almedhychy, Danvers, MA (US); Anjan K. Chakrabarti, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 299 days.

(21) Appl. No.: 17/545,423

(22) Filed: Dec. 8, 2021

(65) Prior Publication Data

US 2022/0184377 A1 Jun. 16, 2022

Related U.S. Application Data

(60) Provisional application No. 63/123,576, filed on Dec. 10, 2020.

(51) Int. Cl.
| | | |
|---|---|---|
| *A61M 60/867* | (2021.01) | |
| *A61M 60/174* | (2021.01) | |
| *A61M 60/216* | (2021.01) | |
| *A61M 60/857* | (2021.01) | |

(52) U.S. Cl.
CPC ........ *A61M 60/867* (2021.01); *A61M 60/174* (2021.01); *A61M 60/216* (2021.01); *A61M 60/857* (2021.01); *A61M 2230/04* (2013.01)

(58) Field of Classification Search
None
See application file for complete search history.

(56) References Cited

U.S. PATENT DOCUMENTS 4,809,681 A * 3/1989 Kantrowitz ......... A61M 60/497
600/521
5,121,750 A * 6/1992 Katims ................. A61B 5/061
600/547

(Continued)

FOREIGN PATENT DOCUMENTS

| CN | 109288642 A | 2/2019 |
|---|---|---|
| EP | 3287154 A1 | 2/2018 |

(Continued)

OTHER PUBLICATIONS

International Preliminary Report on Patentability and Written Opinion for International Application No. PCT/US2021/062407 dated Jun. 22, 2023 (7 pages).

(Continued)

*Primary Examiner* — Carl H Layno
*Assistant Examiner* — Manolis Pahakis
(74) *Attorney, Agent, or Firm* — Botos Churchill IP Law LLP

(57) ABSTRACT

Systems and methods for determining the positioning of intracardiac devices, such as intracardiac blood pump assemblies, using electrical sensors configured to sense electrical potential as it propagates through the heart. In one example, the present technology provides an intracardiac device with one or more electrical sensors mounted thereon, and a controller configured to determine the absolute or relative location of the intracardiac device based on the timing, shape, and/or amplitude of the electrical signals received from the one or more sensors.

11 Claims, 10 Drawing Sheets

(56) References Cited

U.S. PATENT DOCUMENTS

| | | | | |
|---|---|---|---|---|
| 5,174,289 A * | 12/1992 | Cohen | A61N 1/368 | 607/9 |
| 5,570,671 A * | 11/1996 | Hickey | A61B 5/0215 | 600/593 |
| 5,666,958 A * | 9/1997 | Rothenberg | A61N 1/056 | 600/509 |
| 5,738,096 A * | 4/1998 | Ben-Haim | A61N 1/32 | 600/407 |
| 5,840,030 A * | 11/1998 | Ferek-Petric | A61B 18/1492 | 607/122 |
| 5,980,448 A * | 11/1999 | Heilman | A61M 60/876 | 600/16 |
| 6,266,563 B1 * | 7/2001 | KenKnight | A61N 1/3918 | 607/4 |
| 6,544,216 B1 | 4/2003 | Sammler et al. | | |
| 7,546,162 B2 | 6/2009 | Ding et al. | | |
| 7,842,031 B2 | 11/2010 | Abboud et al. | | |
| 7,846,101 B2 | 12/2010 | Eberle et al. | | |
| 9,486,143 B2 | 11/2016 | Hoseit et al. | | |
| 10,029,037 B2 | 7/2018 | Muller et al. | | |
| 11,122,990 B2 * | 9/2021 | Grunwald | A61B 34/20 | |
| 2004/0097805 A1 * | 5/2004 | Verard | A61B 34/20 | 600/428 |
| 2004/0127805 A1 * | 7/2004 | MacAdam | A61B 5/364 | 600/515 |
| 2005/0203368 A1 * | 9/2005 | Verin | A61B 5/06 | 600/407 |
| 2006/0085041 A1 * | 4/2006 | Hastings | A61N 1/37223 | 607/33 |
| 2007/0055141 A1 * | 3/2007 | Kruger | A61B 5/062 | 600/424 |
| 2007/0167801 A1 * | 7/2007 | Webler | G06T 19/00 | 600/459 |
| 2007/0225610 A1 * | 9/2007 | Mickley | A61B 5/287 | 600/509 |
| 2008/0097232 A1 * | 4/2008 | Rothenberg | A61B 5/349 | 600/509 |
| 2009/0005675 A1 * | 1/2009 | Grunwald | A61B 5/283 | 600/467 |
| 2009/0005832 A1 * | 1/2009 | Zhu | A61N 1/3627 | 607/27 |
| 2010/0036227 A1 * | 2/2010 | Cox | A61B 5/283 | 600/509 |
| 2010/0082099 A1 * | 4/2010 | Vodermayer | A61M 60/148 | 600/17 |
| 2010/0240944 A1 * | 9/2010 | Maschke | A61M 60/867 | 600/16 |
| 2010/0317981 A1 * | 12/2010 | Grunwald | A61B 5/349 | 600/509 |
| 2011/0015533 A1 * | 1/2011 | Cox | A61B 5/283 | 600/509 |
| 2011/0196248 A1 * | 8/2011 | Grunwald | A61B 5/063 | 600/509 |
| 2012/0004564 A1 * | 1/2012 | Dobak, III | A61B 5/287 | 600/513 |
| 2012/0046562 A1 * | 2/2012 | Powers | A61B 5/7246 | 600/509 |
| 2012/0059270 A1 * | 3/2012 | Grunwald | A61B 5/352 | 600/509 |
| 2013/0041204 A1 * | 2/2013 | Heilman | A61M 60/531 | 600/17 |
| 2014/0094706 A1 * | 4/2014 | Hedberg | A61B 5/063 | 600/509 |
| 2014/0275720 A1 * | 9/2014 | Ferrari | A61M 60/462 | 600/16 |
| 2015/0202443 A1 | 7/2015 | Zielinski et al. | | |
| 2015/0290372 A1 * | 10/2015 | Muller | A61M 60/174 | 600/16 |
| 2016/0320210 A1 * | 11/2016 | Nelson | A61B 5/062 | |
| 2017/0304634 A1 | 10/2017 | Sanghera et al. | | |
| 2017/0348471 A1 * | 12/2017 | Goto | A61M 5/5086 | |
| 2018/0279897 A1 * | 10/2018 | Eddy | A61B 5/287 | |
| 2019/0076051 A1 * | 3/2019 | Joyce | A61B 5/065 | |
| 2019/0111270 A1 | 4/2019 | Zhou | | |
| 2019/0209755 A1 | 7/2019 | Nix et al. | | |
| 2020/0085343 A1 * | 3/2020 | Nelson | A61B 5/062 | |
| 2020/0196885 A1 * | 6/2020 | Harlev | A61B 5/062 | |
| 2020/0289829 A1 | 9/2020 | Ghosh | | |
| 2020/0330667 A1 | 10/2020 | Fantuzzi et al. | | |
| 2020/0397511 A1 * | 12/2020 | Ishrak | A61F 2/2427 | |
| 2020/0405929 A1 | 12/2020 | Tan et al. | | |
| 2022/0175316 A1 * | 6/2022 | Schmid Daners | A61B 5/322 | |

FOREIGN PATENT DOCUMENTS

| | | |
|---|---|---|
| WO | 2015109071 A1 | 7/2015 |
| WO | 2016086037 A1 | 6/2016 |
| WO | 2020232333 A1 | 11/2020 |
| WO | 2020263962 A1 | 12/2020 |

OTHER PUBLICATIONS

International Search Report and Written Opinion for Application No. PCT/US22/24592 dated Sep. 19, 2022.

Partial Search Report and Provisional Opinion for Application No. PCT/US22/24592 dated Jul. 28, 2022 (13 pages).

International Search Report and Written Opinion for Application No. PCT/US21/062407 dated Mar. 30, 2022 (12 pages).

Office Action from corresponding Taiwan Patent Application No. 110145819 dated Mar. 5, 2025 (10 pp.).

* cited by examiner

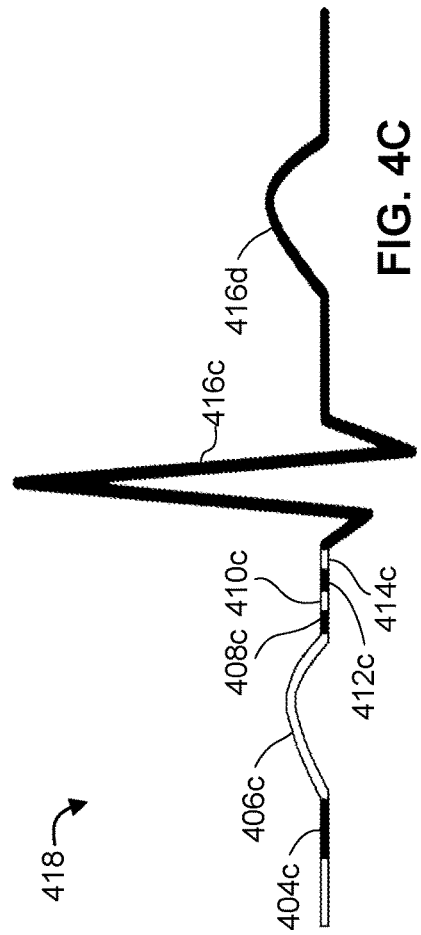
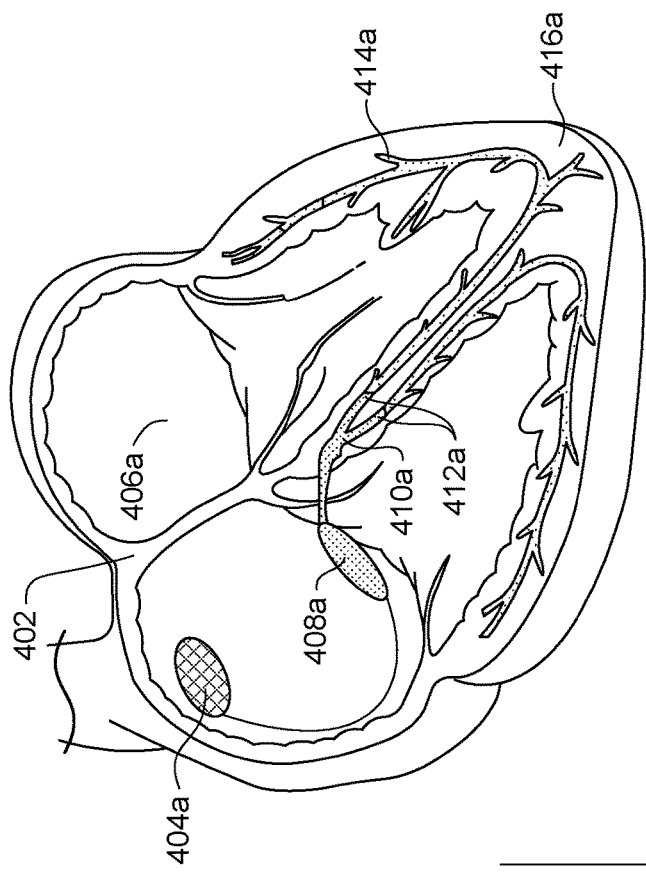
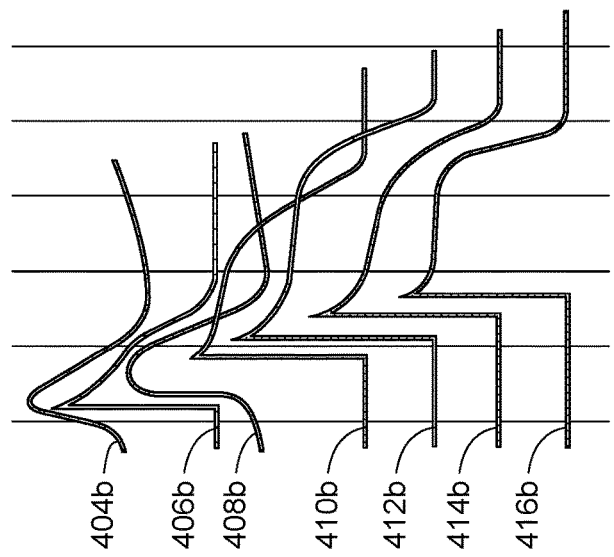

SYSTEMS AND METHODS FOR DETERMINING POSITIONING OF INTRACARDIAC DEVICES

CROSS-REFERENCE TO RELATED APPLICATIONS

The present application claims priority to U.S. Provisional Application No. 63/123,576, filed Dec. 10, 2020, the disclosure of which is incorporated by reference in its entirety.

BACKGROUND

Intracardiac blood pump assemblies can be introduced into the heart either surgically or percutaneously and used to deliver blood from one location in the heart or circulatory system to another location in the heart or circulatory system. For example, when deployed in the left heart, an intracardiac blood pump can pump blood from the left ventricle of the heart into the aorta. Likewise, when deployed in the right heart, an intracardiac blood pump can pump blood from the inferior vena cava into the pulmonary artery. Intracardiac pumps can be powered by a motor located outside of the patient's body via an elongate drive shaft (or drive cable) or by an onboard motor located inside the patient's body. Some intracardiac blood pump systems can operate in parallel with the native heart to supplement cardiac output and partially or fully unload components of the heart. Examples of such systems include the IMPELLA® family of devices (Abiomed, Inc., Danvers Mass.).

Various methods may be used to ensure that an intracardiac blood pump is positioned at a desired location within a patient's heart. For example, after an intracardiac blood pump assembly has been inserted into a patient, various types of medical imaging (e.g., fluoroscopy, echocardiogram, x-ray) may be used to confirm that it has been positioned at a desired location with a patient's heart. However, while medical imaging can help confirm that the intracardiac blood pump assembly is correctly positioned initially, the pump may shift within the patient over time for various reasons. As medical imaging techniques only show the pump's position during a finite window in time, and as many medical imaging techniques are not available at a patient's bedside (e.g., while recovering in an ICU), they are often not practical for monitoring the placement of the blood pump assembly to ensure that it remains in the desired position.

Rather, for ongoing monitoring of the pump's position, pressure sensors may be used. In that regard, a pressure sensor may be affixed to a portion of the intracardiac blood pump assembly, and its readings may be used to determine when that portion of the intracardiac blood pump assembly has passed various segments of the cardiovascular system separated by valves, as such transitions may have telltale pressure gradients and/or pressure fluctuations. However, while a pressure sensor may indicate that the intracardiac blood pump assembly has entered into a particular vessel or cavity, as pressure will be largely uniform within a given vessel or cavity, a pressure sensor may be unable to indicate where the intracardiac blood pump assembly is within that vessel or cavity. For example, a pressure sensor may be able to confirm that the distal end of the intracardiac blood pump assembly has passed through the aortic valve and entered the left ventricle, but due to pressure being largely uniform within the left ventricle, the pressure reading may not allow the operator to conclude whether the tip is positioned at the apical or basal end of the left ventricle, or whether the tip is in the middle of the left ventricle or near a wall of the left ventricle.

BRIEF SUMMARY

The present technology relates to systems and methods for determining the positioning of intracardiac devices, such as intracardiac blood pump assemblies, using electrical sensors. In that regard, one or more electrical sensors mounted on the intracardiac device may be used to sense electrical pulses within a patient's heart. Due to the ways in which electrical potential propagates through the heart during each heartbeat, the absolute or relative shape and/or timing of the electrical signals received from the electrical sensors may be used determine the position of the intracardiac device within the heart. Likewise, the strength of the signals and/or the stability of the signals received from the electrical sensors over time may be used to determine whether the intracardiac device has moved from its initial position. In some aspects, where portions of the intracardiac device are intended to rest against portions of the patient's heart and vasculature when the device is properly positioned, one or more of the electrical sensors may be located at such portions of the device. For example, an intracardiac blood pump may have a cannula with one or more preformed bends based on anatomical features of the heart. In such cases, one or more electrical sensors may be positioned at one or more of the preformed bends in order to determine where the one or more bends are located relative to the patient's anatomy.

In one aspect, the disclosure describes a system for sensing position of an intracardiac device, comprising: an intracardiac device configured to be inserted into a patient's heart; one or more sensors mounted on the intracardiac device and configured to sense electrical pulses within the patient's heart; and one or more processors configured to determine a position of the intracardiac device based at least in part on one or more signals received from the one or more sensors. In some aspects, the one or more sensors comprise a first sensor mounted at a first location on the intracardiac device, and a second sensor mounted at a second location on the intracardiac device. In some aspects, the one or more processors being configured to determine a position of the intracardiac device based at least in part on one or more signals received from the one or more sensors comprises being configured to compare relative shapes of one or more signals received from a first sensor of the one or more sensors, and of one or more signals received from a second sensor of the one or more sensors. Further in that regard, in some aspects, the one or more processors being configured to determine a position of the intracardiac device based at least in part on one or more signals received from the one or more sensors further comprises being configured to compare the relative shapes to data regarding representative heart waves. In some aspects, the one or more processors being configured to determine a position of the intracardiac device based at least in part on one or more signals received from the one or more sensors comprises being configured to compare relative timing of one or more signals received from a first sensor of the one or more sensors, and of one or more signals received from a second sensor of the one or more sensors. Further in that regard, in some aspects, the one or more processors being configured to determine a position of the intracardiac device based at least in part on one or more signals received from the one or more sensors further comprises being configured to compare the relative timing to data regarding representative heart waves. In some aspects, the one or more processors being configured to determine a position of the intracardiac device based at least in part on one or more signals received from the one or more sensors comprises being configured to compare relative amplitudes of one or more signals received from a first sensor of the one or more sensors, and of one or more signals received from a second sensor of the one or more sensors. Further in that regard, in some aspect, the one or more processors being configured to determine a position of the intracardiac device based at least in part on one or more signals received from the one or more sensors further comprises being configured to compare the relative amplitudes to data regarding representative heart waves. In some aspects, the one or more processors being configured to determine a position of the intracardiac device based at least in part on one or more signals received from the one or more sensors comprises being configured to compare one or more signals received from the one or more sensors during a first heartbeat to one or more signals received from the one or more sensors during a second heartbeat. Further in that regard, in some aspects, the one or more processors are further configured to determine a position of the intracardiac device based at least in part on a predetermined position of the intracardiac device within the heart. Further in that regard, in some aspects, the one or more processors being configured to determine a position of the intracardiac device based at least in part on one or more signals received from the one or more sensors comprises being configured to determine whether a difference between the one or more signals received from the one or more sensors during the first heartbeat and the one or more signals received from the one or more sensors during the second heartbeat indicates that the intracardiac device has moved from the predetermined position. In some aspects, the intracardiac device comprises an intracardiac blood pump.

In another aspect, the disclosure describes a method of determining position of an intracardiac device, comprising: inserting an intracardiac device into a patient's heart, the intracardiac device having one or more sensors configured to sense electrical pulses within the patient's heart; receiving one or more signals received from the one or more sensors; and determining, with one or more processors of a processing system, a position of the intracardiac device based at least in part on the one or more signals received from the one or more sensors. In some aspects, the one or more signals from the one or more sensors comprise a first signal received from a first sensor during a heartbeat, and a second signal received from a second sensor during the heartbeat. In some aspects, the one or more signals from the one or more sensors comprise a first signal received from a first sensor during a first heartbeat, and a second signal received from the first sensor during a second heartbeat. In some aspects, determining a position of the intracardiac device based at least in part on the one or more signals received from the one or more sensors comprises comparing relative shapes of one or more signals received from a first sensor of the one or more sensors, and of one or more signals received from a second sensor of the one or more sensors. Further in that regard, in some aspects, determining a position of the intracardiac device based at least in part on the one or more signals received from the one or more sensors further comprises comparing the relative shapes to data regarding representative heart waves. In some aspects, determining a position of the intracardiac device based at least in part on the one or more signals received from the one or more sensors comprises comparing relative timing of one or more signals received from a first sensor of the one or more sensors, and of one or more signals received from a second sensor of the one or more sensors. Further in that regard, in some aspects, determining a position of the intracardiac device based at least in part on the one or more signals received from the one or more sensors further comprises comparing the relative timing to data regarding representative heart waves. In some aspects, determining a position of the intracardiac device based at least in part on the one or more signals received from the one or more sensors comprises comparing relative amplitudes of one or more signals received from a first sensor of the one or more sensors, and of one or more signals received from a second sensor of the one or more sensors. Further in that regard, in some aspects, determining a position of the intracardiac device based at least in part on the one or more signals received from the one or more sensors further comprises comparing the relative amplitudes to data regarding representative heart waves. In some aspects, determining a position of the intracardiac device based at least in part on the one or more signals received from the one or more sensors comprises comparing one or more signals received from the one or more sensors during a first heartbeat to one or more signals received from the one or more sensors during a second heartbeat. Further in that regard, in some aspects, determining a position of the intracardiac device is further based at least in part on a predetermined position of the intracardiac device within the heart. Further in that regard, in some aspects, determining a position of the intracardiac device based at least in part on the one or more signals received from the one or more sensors comprises determining whether a difference between the one or more signals received from the one or more sensors during the first heartbeat and the one or more signals received from the one or more sensors during the second heartbeat indicates that the intracardiac device has moved from the predetermined position. In some aspects, the intracardiac device comprises an intracardiac blood pump.

BRIEF DESCRIPTION OF DRAWINGS

FIG. 4A shows a partial sectional view of a human heart, and selected portions of the heart's electrical conduction system;

FIG. 4B is a graph illustrating the general timing and shape of electrical waves that may be sensed at various points in the electrical conduction system during a typical heartbeat;

FIG. 4C is a graph illustrating a typical ECG signal, and identifying the portion thereof attributable to each of the waves identified in FIG. 4B;

DETAILED DESCRIPTION

Figure 1:
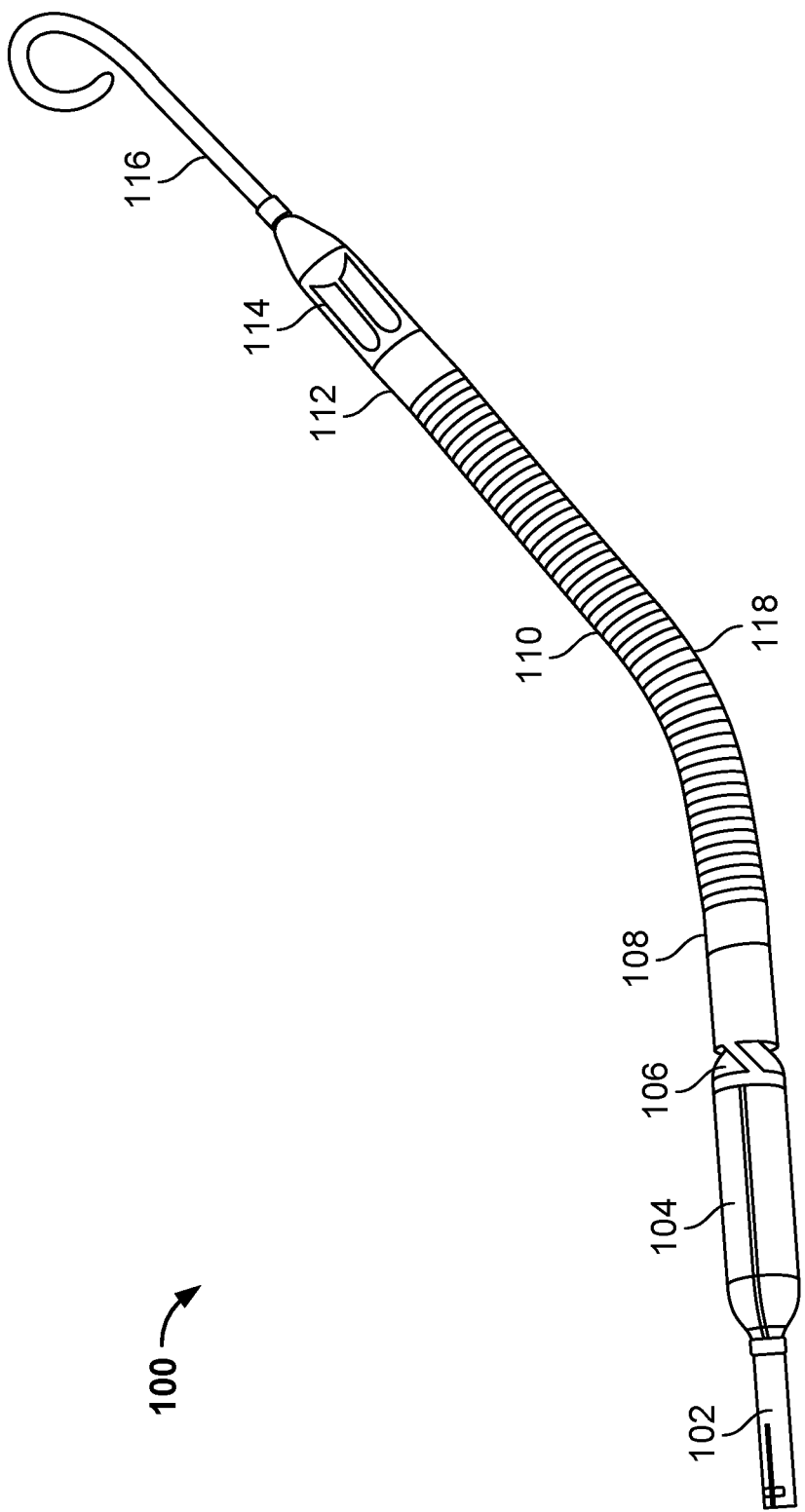
FIG. 1 depicts an exemplary intracardiac blood pump assembly configured for left heart support, in accordance with aspects of the disclosure.

Embodiments of the present disclosure are described in detail with reference to the figures wherein like reference numerals identify similar or identical elements. It is to be understood that the disclosed embodiments are merely examples of the disclosure, which may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

To provide an overall understanding of the systems, methods, and devices described herein, certain illustrative embodiments will be described. Although the embodiments and features described herein are specifically described for use in connection with an intracardiac blood pump system, it will be understood that all the components and other features outlined below may be combined with one another in any suitable manner and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based introduced catheters and devices.

The systems, methods, and devices described herein allow for the position of an intracardiac device to be determined by sensing the heart's own electrical signals using one or more sensors mounted on the intracardiac device. The present technology thus allows position be determined and/or maintained based on the absolute or relative shape and/or timing of the electrical signals sensed by the electrical sensors, the strength of the signals, the stability of the signals over time, etc. In that regard, the present technology beneficially allows position to be determined and/or maintained at specific positions within ventricles or other portions of the patient's heart and vasculature where doing so with pressure sensors may not be feasible.

FIG. 1 depicts an exemplary intracardiac blood pump assembly 100 adapted for left heart support. In that regard, the intracardiac blood pump assembly 100 includes an elongate catheter 102, a motor 104, a cannula 110, a blood inflow cage 114 arranged at or near the distal end 112 of the cannula 110, a blood outflow cage 106 arranged at or near the proximal end 108 of the cannula 110, and an optional atraumatic extension 116 arranged at the distal end of the blood inflow cage 114.

Motor 104 is configured to rotatable drive an impeller (not shown), thereby generating suction sufficient to draw blood into cannula 110 through the blood inflow cage 114, and to expel the blood out of cannula 110 through the blood outflow cage 106. In that regard, the impeller may be positioned distal of the blood outflow cage 106, for example, within the proximal end 108 of the cannula 110 or within a housing coupled to the proximal end 108 of the cannula 110. In some aspects of the technology, rather than the impeller being driven by an in-dwelling motor 104, the impeller may instead be coupled to an elongate drive shaft (or drive cable) which is driven by a motor located external to the patient.

Catheter 102 may house electrical lines coupling the motor 104 to one or more electrical controllers or other sensors. Alternatively, where the impeller is driven by an external motor, an elongate drive shaft may pass through catheter 102. Catheter 102 may also serve as a conduit for wires connecting the electrical sensors described further below to one or more controllers, power sources, etc. located outside the patient's body. Catheter 102 may also include a purge fluid conduit, a lumen configured to receive a guidewire, etc.

The blood inflow cage 114 includes one or more apertures or openings configured to allow blood to be drawn into cannula 110 when the motor 104 is operating. Likewise, blood outflow cage 106 includes one or more apertures or openings configured to allow blood to flow from the cannula 110 out of the intracardiac blood pump assembly 100. Blood inflow cage 114 and outflow cage 106 may be composed of any suitable bio-compatible material(s). For example, blood inflow cage 114 and/or blood outflow cage 106 may be formed out of bio-compatible metals such as stainless steel, titanium, or biocompatible polymers such as polyurethane. In addition, the surfaces of blood inflow cage 114 and/or blood outflow cage 106 may be treated in various ways, including, but not limited to etching, texturing, or coating or plating with another material. For example, the surfaces of blood inflow cage 114 and/or blood outflow cage 106 may be laser textured.

Cannula 110 may include a flexible hose portion. For example, cannula 110 may be composed, at least in part, of a polyurethane material. In addition, cannula 110 may include a shape-memory material. For example, cannula 110 may comprise a combination of a polyurethane material and one or more strands or coils of a shape-memory material such as Nitinol. Cannula 110 may be formed such that it includes one or more bends or curves in its relaxed state, or it may be configured to be straight in its relaxed state. In that regard, in the exemplary arrangement shown in FIG. 1, the cannula 110 has a single pre-formed anatomical bend 118 based on the portion of the left heart in which it is intended to operate. Despite this bend 118, the cannula 110 may nevertheless also be flexible, and may thus be capable of straightening (e.g., during insertion over a guidewire), or bending further (e.g., in a patient whose anatomy has tighter dimensions). Further in that regard, cannula 110 may include a shape-memory material configured to allow the cannula 110 to be a different shape (e.g., straight or mostly straight)

at room temperatures, and to form bend 118 once the shape-memory material is exposed to the heat of a patient's body.

Atraumatic extension 116 assists with stabilizing and positioning the intracardiac blood pump assembly 100 in the correct position in the patient's heart. Atraumatic extension 116 may be solid or tubular. If tubular, atraumatic extension 116 may be configured to allow a guidewire to be passed through it to further assist in the positioning of the intracardiac blood pump assembly 100. Atraumatic extension 116 may be any suitable size. For example, atraumatic extension 116 may have an outer diameter in the range of 4-8 Fr. Atraumatic extension 116 may be composed, at least in part, of a flexible material, and may be any suitable shape or configuration such as a straight configuration, a partially curved configuration, a pigtail-shaped configuration as shown in the example of FIG. 1, etc. Atraumatic extension 116 may also have sections with different stiffnesses. For example, atraumatic extension 116 may include a proximal section that is stiff enough to prevent it from buckling, thereby keeping the blood inflow cage 114 in the desired location, and a distal section that is softer and has a lower stiffness, thereby providing an atraumatic tip for contact with a wall of the patient's heart and to allow for guidewire loading. In other cases, the atraumatic extension 116 may have a distal section that is stiffer than a proximal section. In all cases, individual sections of the atraumatic extension 116 may be composed of different materials, or may be composed of the same material, treated to provide different stiffnesses.

Notwithstanding the foregoing, as mentioned above, atraumatic extension 116 is an optional structure. In that regard, the present technology may also be used with intracardiac blood pump assemblies and other intracardiac devices that include extensions of different types, shapes, materials, and qualities. Likewise, the present technology may be used with intracardiac blood pump assemblies and other intracardiac devices that have no distal extensions of any kind.

Intracardiac blood pump assembly 100 may be inserted percutaneously or using minimally invasive surgical techniques. For example, when used for left heart support, intracardiac blood pump assembly 100 may be inserted via a catheterization procedure through the femoral artery or axillary artery, into the aorta, across the aortic valve, and into the left ventricle. Once positioned in this way, the intracardiac blood pump assembly 100 delivers blood from the blood inflow cage 114, which sits inside the left ventricle, through cannula 110, to the blood outflow cage 106, which sits inside the ascending aorta. As will be explained further below, in some aspects of the technology, intracardiac blood pump assembly 100 may be configured such that bend 118 will rest against a predetermined portion of the patient's heart when the intracardiac blood pump assembly 100 is in a desired location. Likewise, the atraumatic extension 116 may be configured such that it rests against a different predetermined portion of the patient's heart when the intracardiac blood pump assembly 100 is in the desired location.

Figure 2:
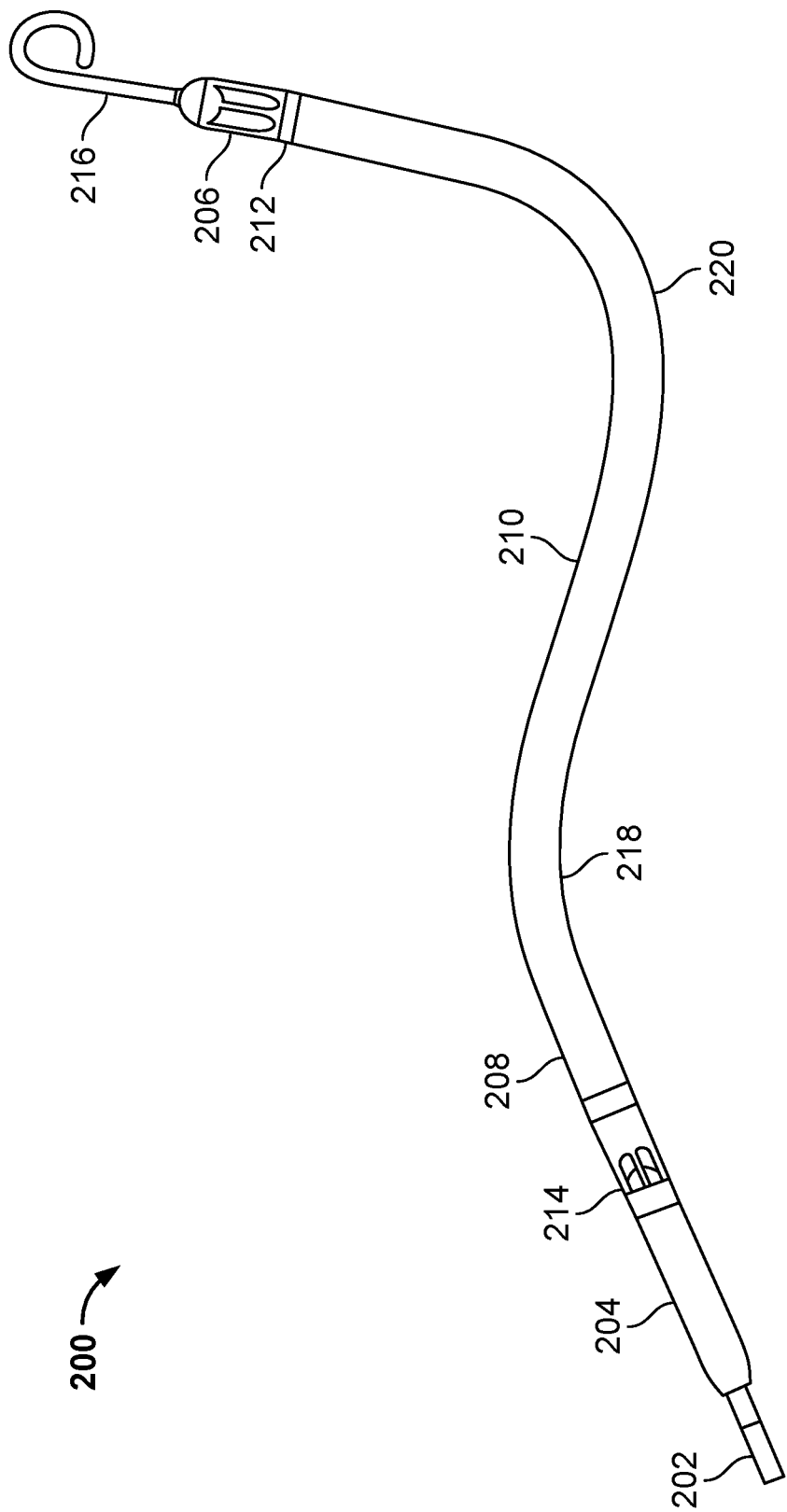
FIG. 2 depicts an exemplary intracardiac blood pump assembly configured for right heart support, in accordance with aspects of the disclosure.

FIG. 2 depicts an exemplary intracardiac blood pump assembly 200 adapted for right heart support. In that regard, the intracardiac blood pump assembly 200 includes an elongate catheter 202, a motor 204, a cannula 210, a blood inflow cage 214 arranged at or near the proximal end 208 of the cannula 210, a blood outflow cage 206 arranged at or near the distal end 212 of the cannula 210, and an optional atraumatic extension 216 arranged at the distal end of the blood outflow cage 206.

As with the exemplary assembly of FIG. 1, motor 204 is configured to rotatable drive an impeller (not shown), thereby generating suction sufficient to draw blood into cannula 210 through the blood inflow cage 214, and to expel the blood out of cannula 210 through the blood outflow cage 206. In that regard, the impeller may be positioned distal of the blood inflow cage 214, for example, within the proximal end 208 of the cannula 210 or within a housing coupled to the proximal end 208 of the cannula 210. Here as well, in some aspects of the technology, rather than the impeller being driven by an in-dwelling motor 204, the impeller may instead be coupled to an elongate drive shaft (or drive cable) which is driven by a motor located external to the patient.

The cannula 210 of FIG. 2 serves the same purpose, and may have the same properties and features described above with respect to cannula 110 of FIG. 1. However, in the exemplary arrangement shown in FIG. 2, the cannula 210 has two pre-formed anatomical bends 218 and 220 based on the portion of the right heart in which it is intended to operate. Here again, despite the existence of bends 218 and 220, the cannula 210 may nevertheless also be flexible, and may thus be capable of straightening (e.g., during insertion over a guidewire), or bending further (e.g., in a patient whose anatomy has tighter dimensions). Further in that regard, cannula 210 may include a shape-memory material configured to allow the cannula 210 to be a different shape (e.g., straight or mostly straight) at room temperatures, and to form bends 218 and/or 220 once the shape-memory material is exposed to the heat of a patient's body.

The catheter 202 and atraumatic extension 216 of FIG. 2 serve the same purpose and may have the same properties and features described above with respect to catheter 102 and atraumatic extension 116 of FIG. 1. Likewise, other than being located at opposite ends of the cannula from those of FIG. 1, the blood inflow cage 214 and blood outflow cage 206 of FIG. 2 are similar to the blood inflow cage 114 and blood outflow cage 106 of FIG. 1, and thus may have the same properties and features described above.

Like the exemplary assembly of FIG. 1, the intracardiac blood pump assembly 200 of FIG. 2 may also be inserted percutaneously or using minimally invasive surgical techniques. For example, when used for right heart support, intracardiac blood pump assembly 200 may be inserted via a catheterization procedure through the femoral vein, into the inferior vena cava, through the right atrium, across the tricuspid valve, into the right ventricle, through the pulmonary valve, and into the pulmonary artery. Once positioned in this way, the intracardiac blood pump assembly 200 delivers blood from the blood inflow cage 214, which sits inside the inferior vena cava, through cannula 210, to the blood outflow cage 206, which sits inside the pulmonary artery.

Figure 3:
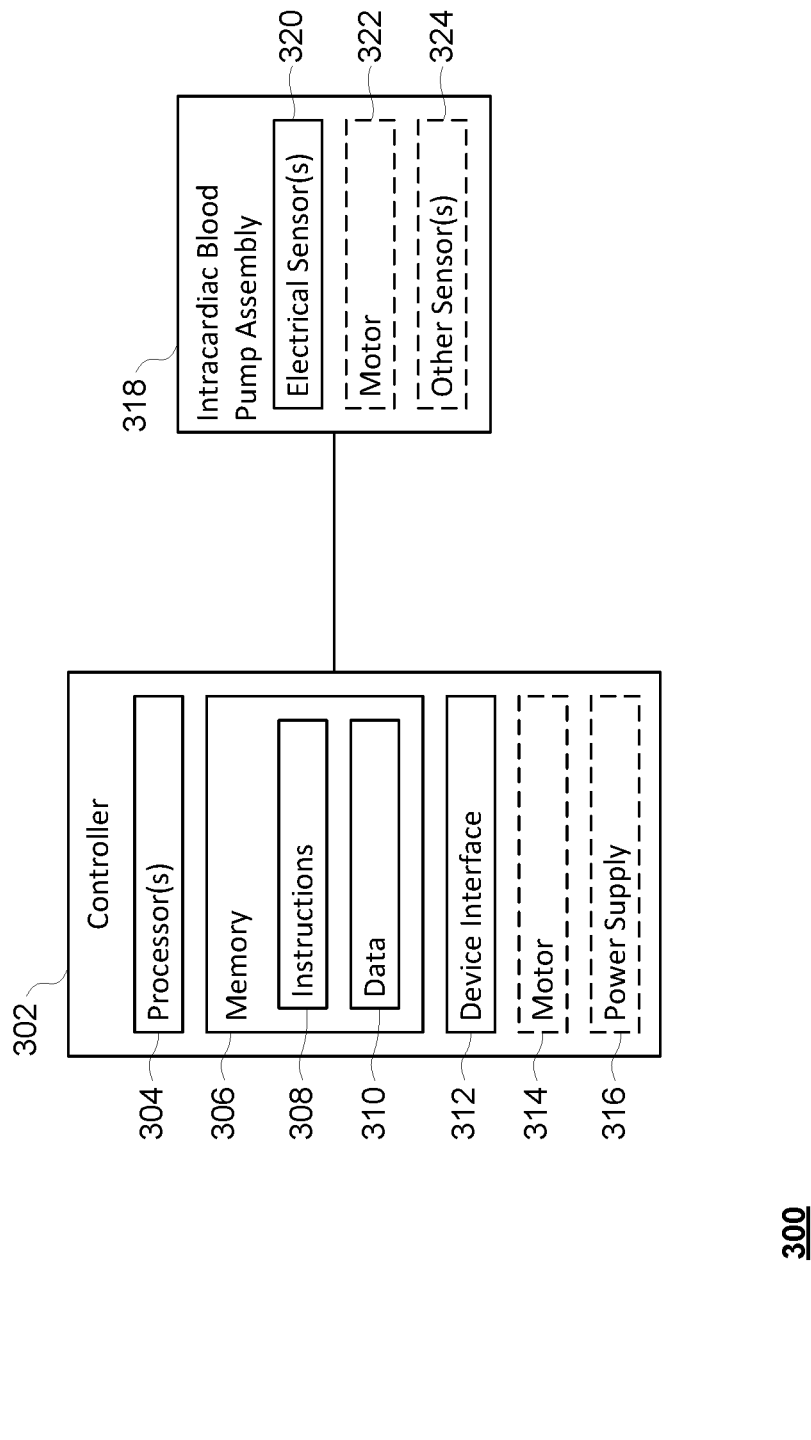
FIG. 3 is a functional block diagram of an exemplary intracardiac blood assembly in accordance with aspects of the disclosure.

FIG. 3 is a functional block diagram of an exemplary system in accordance with aspects of the disclosure. In that regard, in the example of FIG. 3, the system 300 comprises an intracardiac blood pump assembly 318 and a controller 302. The intracardiac blood pump assembly 318 may take any form, including those shown in the exemplary blood pump assemblies 100 and 200 of FIG. 1 or 2, respectively. In addition, the intracardiac blood pump assembly 318 of FIG. 3 includes one or more electrical sensors 320, which may be configured to sense electrical potential within a patient's heart as discussed further above and below. The intracardiac blood pump assembly 318 may also optionally include a motor 322 configured to rotatably drive an impeller (e.g., in instances where the motor is configured to be inserted into the patient) and/or one or more additional sensors 324 (e.g., pressure sensors, temperature sensors, kink sensors, etc.). Notwithstanding the foregoing, the present technology may also be employed in systems comprising an intracardiac device other than a blood pump assembly.

In the example of FIG. 3, the controller 302 includes one or more processors 304 coupled to memory 306 storing instructions 308 and data 310, and an interface 312 with the intracardiac blood pump assembly 318. Controller 302 may additionally include an optional motor 314 (e.g., in instances where the impeller is driven by a motor located external to the patient via an elongate drive shaft) and/or a power supply 316 (e.g., to power an in-dwelling motor 322, electrical sensors 320, etc.). The interface 312 with intracardiac blood pump assembly 318 may be any suitable interface. In that regard, interface 312 may be configured to enable one one-way or two-way communication between the controller 302 and the intracardiac blood pump assembly 318. Interface 312 may further be configured to provide power to the one or more electrical sensors 320, motor 322, and/or one or more other sensors 324.

Controller 302 may take any form. In that regard, controller 302 may comprise a single modular unit, or its components may be distributed between two or more physical units. Controller 302 may further include any other components normally used in connection with a computing device such as a user interface. In that regard, controller 302 may have a user interface that includes one or more user inputs (e.g., buttons, touchscreen, keypad, keyboard, mouse, microphone, etc.); one or more electronic displays (e.g., a monitor having a screen or any other electrical device that is operable to display information, one or more lights, etc.); one or more speakers, chimes or other audio output devices; and/or one or more other output devices such as vibrating, pulsing, or haptic elements.

The one or more processors 304 and memory 306 described herein may be implemented on any type of computing device(s), including customized hardware or any type of general computing device. Memory 306 may be of any non-transitory type capable of storing information accessible by the processor(s) 304, such as a hard-drive, memory card, optical disk, solid-state, tape memory, or similar structure.

Instructions 308 may include programming configured to receive readings from the electrical sensors 320 and determine the positions of one or more of the electrical sensors 320.

Data 310 may include data for calibrating and/or interpreting the signals of the electrical sensors 320, as well as data regarding representative heart waves (e.g., those exemplified in the illustrative diagram of FIG. 4). Controller 302 may further be configured to store past readings from sensors 320 in memory 306, e.g., for use in determining if the intracardiac device has shifted relative to its initial position.

FIG. 4A is an illustration of a sectional view of a human heart, identifying selected portions of the heart's electrical conduction system. FIG. 4B is a graph illustrating the general timing and shape of electrical waves that may be sensed at each of those selected points in the electrical conduction system during a typical heartbeat. FIG. 4C is a graph illustrating a typical ECG signal, and identifying which portion of that signal is attributable to each of the waves identified in FIG. 4B.

In that regard, in the exemplary human heart 402 of FIG. 4A, element 404a identifies the sinoatrial node, or SA node, which is a group of cells in the wall of the right atrium of the heart which produce the electrical impulse that causes the heart to contract during each heartbeat. The SA node thus produces the rhythm of the heart, and is known as the heart's pacemaker. FIG. 4B includes an illustrative graph 404b showing the general shape and timing of the electrical signal that may be sensed at the SA node during a typical heartbeat. In addition, the SA node's contribution to the full ECG signal 418 of FIG. 4C is shown by the portion identified as 404c.

The electrical impulse produced by the SA node propagates through the conduction system of the heart 402 as a wave of excitation which causes a change in cell membrane potential referred to as depolarization. This change in electrical potential can be sensed by electrical sensors, such as those described herein. In normal circumstances, the depolarization front caused by the SA node's impulse will reach the atrial muscle before it reaches the ventricular muscle. In that regard, element 406a of FIG. 4A generally identifies the atrial muscle, and the illustrative graph 406b of FIG. 4B shows the general shape and timing of the electrical signal that may be sensed at the atrial muscle during a typical heartbeat. In addition, the atrial muscle's contribution to the full ECG signal 418 of FIG. 4C is shown by the portion identified as 406c. This portion 406c of ECG signal 418 is also known as the P wave, and represents the summation of the electrical potential generated by the depolarization front as it propagates through the atria.

The atrioventricular node, or AV node, is activated as the depolarization front spreads out from the SA node through the atria. Upon receiving the impulse (and after imposing a very brief delay), the AV node conducts that electrical impulse to the ventricles. The AV node is located at the center of Koch's triangle, which is defined by the septal leaflet of the tricuspid valve, the coronary sinus, and the membranous part of the interatrial septum. The AV node is identified in FIG. 4A by element 408a, and the illustrative graph 408b of FIG. 4B shows the general shape and timing of the electrical signal that may be sensed at the AV node during a typical heartbeat. In addition, the AV node's contribution to the full ECG signal 418 of FIG. 4C is shown by the portion identified as 408c.

The His bundle is activated by the AV node, and transmits the impulse to the right and left bundle branches. In that regard, element 410a of FIG. 4A identifies the His bundle, and the illustrative graph 410b of FIG. 4B shows the general shape and timing of the electrical signal that may be sensed at the His bundle during a typical heartbeat. In addition, the His bundle's contribution to the full ECG signal 418 of FIG. 4C is shown by the portion identified as 410c.

The left and right bundle branches are activated by the His bundle, and transmit the impulse to the Purkinje fibers. In that regard, element 412a of FIG. 4A identifies the right and left bundle branches, and the illustrative graph 412b of FIG. 4B shows the general shape and timing of the electrical signal that may be sensed at a bundle branch during a typical heartbeat. In addition, the bundle branches' contribution to the full ECG signal 418 of FIG. 4C is shown by the portion identified as 412c.

The Purkinje fibers are located in the inner ventricular walls of the heart, and are activated by the left and right bundle branches. The Purkinje fibers and are what ultimately provide electrical conduction to the myocardium of the ventricles, causing the muscle tissue of the ventricles to contract. In that regard, element 414a of FIG. 4A identifies an exemplary Purkinje fiber, and the illustrative graph 414b of FIG. 4B shows the general shape and timing of the electrical signal that may be sensed at a Purkinje fiber during a typical heartbeat. In addition, the Purkinje fibers' contribution to the full ECG signal 418 of FIG. 4C is shown by the portion identified as 414c.

As noted, the ventricular muscle is activated by the Purkinje fibers. This produces a depolarization front to propagate through the ventricular muscle cells, causing the ventricular muscle to contract and eject blood away from the heart chamber(s). More specifically, the left ventricular areas first excited are the anterior and posterior paraseptal wall and the central left surface of the interventricular septum, while the last part of the left ventricle to be activated is the posterobasal area. Although these specific areas are not called out in the exemplary heart 402 of FIG. 4A, element 416a generally identifies the ventricular muscle, and the illustrative graph 416b of FIG. 4B shows the general shape and timing of the electrical signal that may be sensed at the ventricular muscle during a typical heartbeat. The ventricular muscle's contribution to the full ECG signal 418 of FIG. 4C is shown by the portion identified as 416c and 416d. Portion 416c of ECG signal 418 is also known as the QRS wave, and represents the summation of the electrical potential generated by the depolarization front as it propagates through the ventricular muscle. In addition, as shown by 416d, a further electrical signal known as a T wave can be sensed shortly after the QRS wave. The T wave represents the summation of the electrical potential generated during the repolarization of the ventricular muscle cells, which occurs after contraction.

As can be seen from the illustrative diagrams of FIGS. 4B and 4C, the intracardiac potentials that can be sensed at each of the highlighted portions of the heart will differ in timing, amplitude, and shape. Thus, as will be explained further below, by placing one or more electrical sensors on an intracardiac device, these intracardiac electrocardiographic signatures can be used to determine and monitor the absolute or relative location the intracardiac device in a patient's heart.

Figure 5:
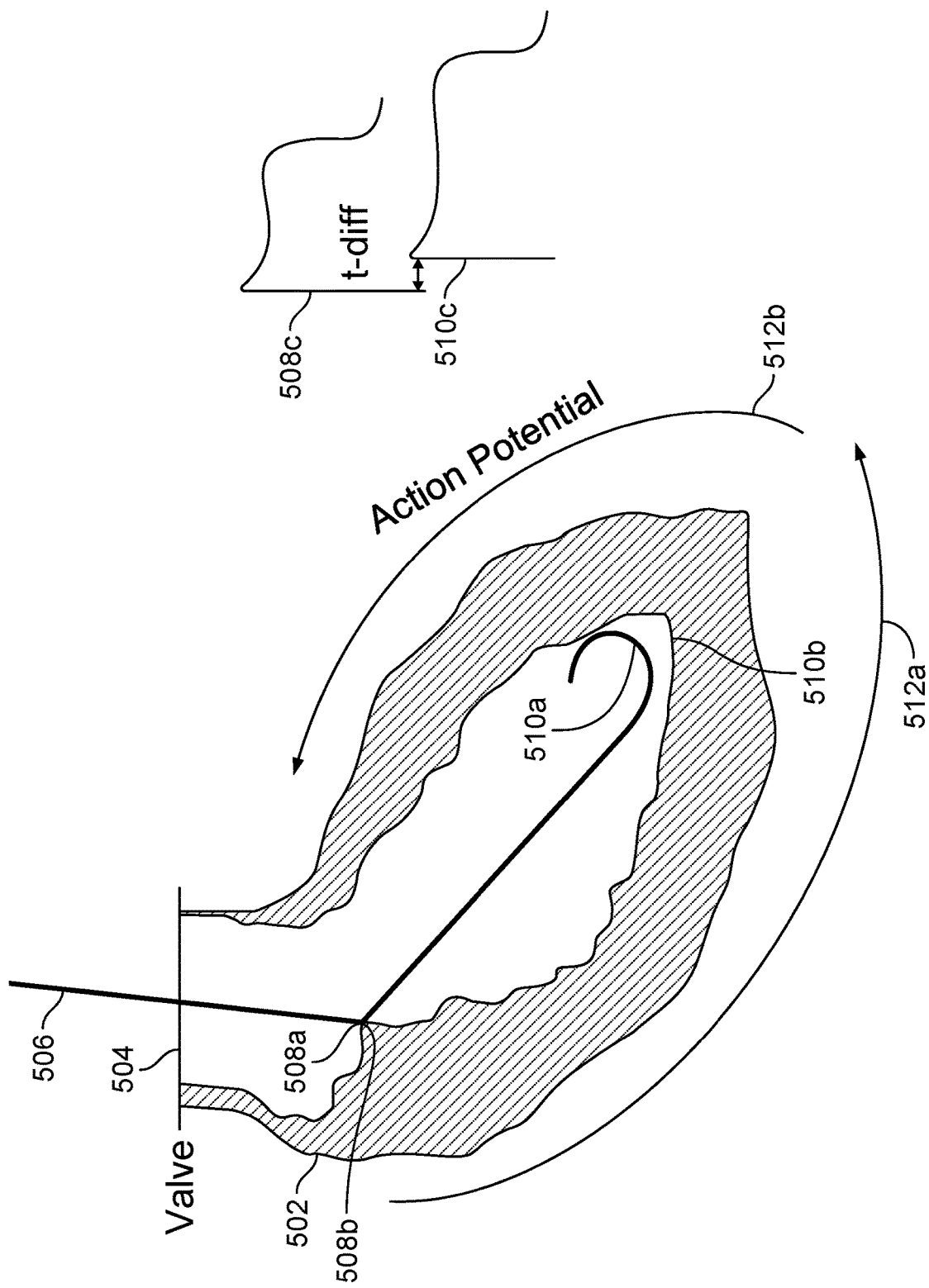
FIG. 5 depicts an intracardiac blood pump assembly inserted into a left ventricle, and illustrates how different electrical signals may be received from sensors placed at different locations on the blood pump assembly, in accordance with aspects of the disclosure.

FIG. 5 depicts a cross-sectional view of a left ventricle 502, with an exemplary intracardiac blood pump assembly 506 inserted therein, in accordance with aspects of the disclosure. FIG. 5 also includes exemplary graphs illustrating how electrical sensors mounted on intracardiac blood pump assembly 506 may produce readings that can be used to determine a location of the intracardiac blood pump assembly 506 within the left ventricle 502.

In the example of FIG. 5, the intracardiac blood pump assembly 506 is configured with electrical sensors 508a and 510a capable of sensing the electrical potential propagating through the heart during each heartbeat as described above with respect to FIG. 5. Electrical sensor 508a is located at a bend in the intracardiac blood pump assembly 506. In that regard, electrical sensor 508a may be located on whatever portion of the bend (e.g., outside of the bend, inside of the bend, side of the bend) will position it optimally relative to the portion of the heart to be sensed. Electrical sensor 510a is located on an atraumatic extension at the distal end of the intracardiac blood pump assembly 506. For the purposes of explanation, it will be assumed that FIG. 5 shows the intracardiac blood pump assembly 506 in a desired position in which it has been inserted through the aortic valve 504, and has come to rest with its bend positioned adjacent a first portion 508b of the left ventricle 502, and its atraumatic extension positioned adjacent a second portion 510b of the left ventricle 502. In some aspects of the technology, the size and shape of the intracardiac blood pump assembly 506 may be configured such that when it has been positioned in this way, the bend and the atraumatic extension of the intracardiac blood pump assembly 506 will rest against these portions 508b and 510b and thus help anchor the intracardiac blood pump assembly 506 within the left ventricle 502. It should be noted that the exact positions of portions 508b and 510b used herein are merely illustrative. As such, in some aspects of the technology, the intracardiac blood pump assembly 506 may be configured such that it will rest against other portions of the anatomy such as the aortic valve, portions of the aorta, etc.

Arrows 512a and 512b illustrate the direction in which electrical potential will propagate through the left ventricle 502. In that regard, as the depolarization front will reach portion 508b before it reaches 510b in a given heartbeat, there will be a time difference between the signals sensed by electrical sensors 508a and 510a. For example, electrical sensors 508a and 510a may produce signals represented by the illustrative graphs 508c and 510c, respectively, which are offset by some time differential. A controller (e.g., controller 302) may be configured to compare the signals from electrical sensors 508a and 510a to determine whether the intracardiac blood pump assembly 506 is in the desired position. In some aspects of the technology, the position of the intracardiac blood pump assembly 506 may be determined based (in whole or in part) on the time difference between the signals from electrical sensors 508a and 510a during a heartbeat. For example, if the time difference is too small, it may indicate that the intracardiac blood pump assembly 506 has folded back on itself such that the atraumatic tip is resting near the first portion 508b of the left ventricle 502. Likewise, if the time difference is too big, it may indicate that the intracardiac blood pump assembly 506 has become kinked such that the atraumatic extension is wedged against the wall opposite the first portion 508b of the left ventricle 502.

Likewise, in some aspects of the technology, the position of the intracardiac blood pump assembly 506 may be determined based (in whole or in part) on changes in the time difference between the signals from electrical sensors 508a and 510a during successive heartbeats. In that regard, if the time difference between the signals from electrical sensors 508a and 510a is relatively stable for a period of time, it may be inferred that the intracardiac blood pump assembly has not shifted relative to its original position (e.g., a position that was initially confirmed in the operating room using medical imaging). On the other hand, if the time difference between the signals from electrical sensors 508a and 510a 506 changes after some period of time, it may be inferred that the intracardiac blood pump assembly has shifted from its original position within the patient's heart. For example, the position of the intracardiac blood pump assembly 506 may be confirmed to match the positioning shown in FIG. 5 using medical imaging immediately after insertion, and a time difference of x milliseconds may be observed between the signals from electrical sensors 508a and 510a during each heartbeat. That time difference of x milliseconds may be used as a standard by which to determine whether the intracardiac blood pump assembly 506 remains in that position once the patient has been moved to an ICU bed, and medical imaging is no longer available. In that regard, a controller (e.g., controller 302) may be configured to determine that the intracardiac blood pump assembly 506 has shifted positions if the time difference in the sensed signals deviates from x by some predetermined amount y, or some predetermined percentage z, etc.

Likewise, in some aspects of the technology, the position of the intracardiac blood pump assembly 506 may be determined based on the presence or absence of signals from electrical sensors 508a and 510a during successive heartbeats. In that regard, if one or both of electrical sensors 508a and 510a fail to produce a signal, it may indicate that the intracardiac blood pump assembly 506 has shifted such that one or both of the sensors are no longer in proximity to their intended anchor points and/or that a portion of the intracardiac blood pump assembly 506 has passed out of the heart.

Further, in some aspects of the technology, the position of the intracardiac blood pump assembly 506 may be determined based (in whole or in part) on the amplitude of the signals from electrical sensors 508a and 510a during a heartbeat. For example, if the difference in the amplitudes of the signals from electrical sensors 508a and 510a is very small (e.g., below some predetermined threshold x), it may indicate that the intracardiac blood pump assembly 506 has folded back on itself such that the atraumatic tip is resting near the first portion 508b of the left ventricle 502. Likewise, if the difference in amplitudes between the two signals is very large (e.g., above some predetermined threshold y), it may indicate that the intracardiac blood pump assembly 506 has become kinked such that the atraumatic extension is wedged against the wall opposite the first portion 508b of the left ventricle 502. Large differences in amplitude may also indicate that one of the sensors has moved through the aortic valve 504 and is sensing a different portion of the ECG signal.

Further, in some aspects of the technology, the position of the intracardiac blood pump assembly 506 may be determined based (in whole or in part) on the shape of the signals from electrical sensors 508a and 510a during a heartbeat. For example, if the differences between the shapes of the signals from electrical sensors 508a and 510a are very small (e.g., as assessed using statistical analyses such as dynamic time warping, Fréchet distance, etc.), it may indicate that the intracardiac blood pump assembly 506 has folded back on itself such that the atraumatic tip is resting near the first portion 508b of the left ventricle 502. Likewise, if the differences between shapes of the two signals are very large (e.g., as assessed using statistical analyses such as dynamic time warping, Fréchet distance, etc.), it may indicate that the intracardiac blood pump assembly 506 has become kinked such that the atraumatic extension is wedged against the wall opposite the first portion 508b of the left ventricle 502. Differing shapes may also indicate that one of the sensors has moved through the aortic valve 504 and is sensing a different portion of the ECG signal. In addition, as typical shapes of ECG signals are generally known, the controller (e.g., controller 302) may be configured to compare the shape of one or both of the signals from electrical sensors 508a and 510a to the shape of an expected ECG signal in order to determine where electrical sensors 508a and 510a must be within the heart. This may be accomplished, for example, using computer modeling, neural networks trained to recognize ECG signals, etc.

Figure 6:
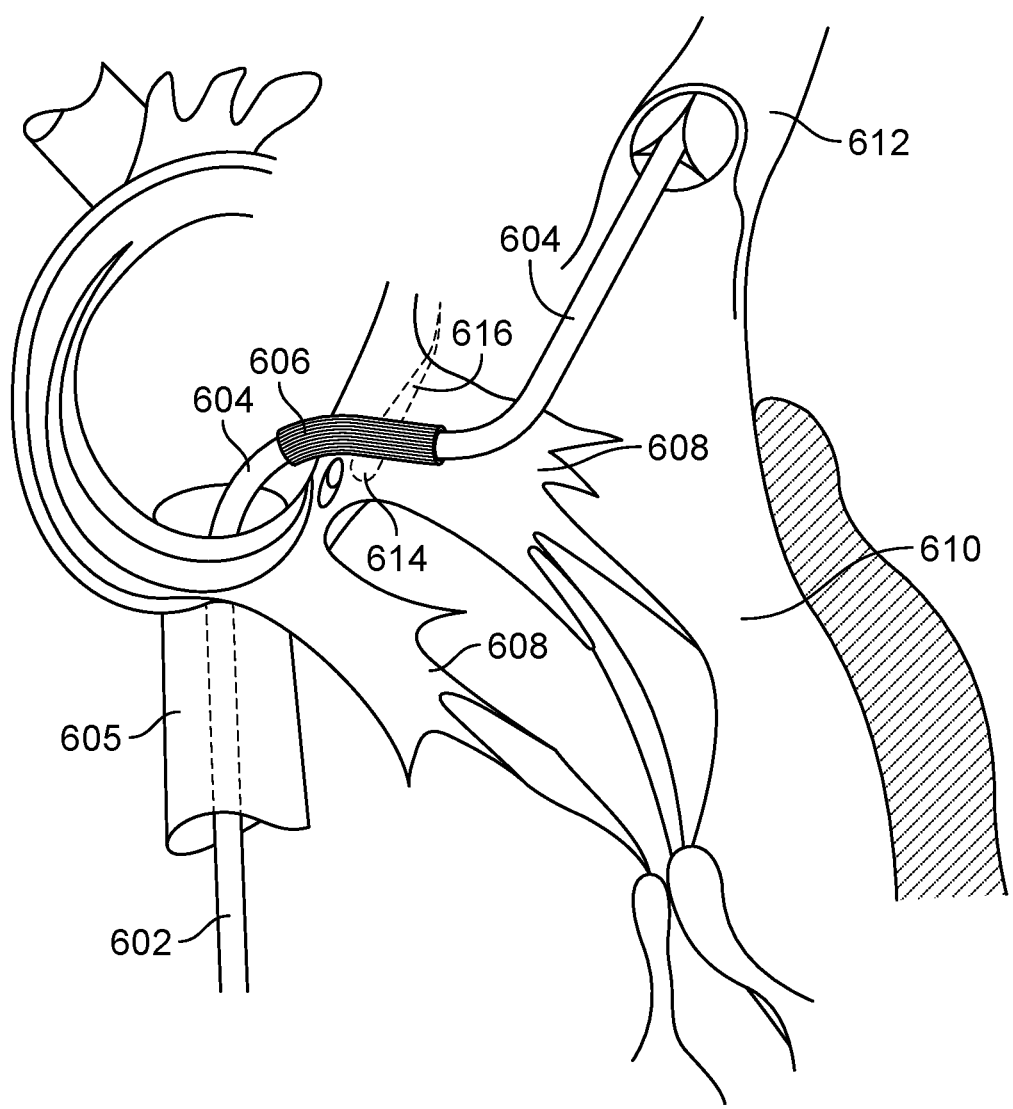
FIG. 6 depicts an intracardiac blood pump assembly inserted into a right ventricle, in accordance with aspects of the disclosure.

FIG. 6 depicts a cross-sectional view of a right ventricle, with an exemplary intracardiac blood pump assembly 602 inserted therein, in accordance with aspects of the disclosure. More specifically, FIG. 6 shows intracardiac blood pump assembly 602 inserted through the inferior vena cava 605, across the paraseptal leaflets 608 of the tricuspid valve, into the right ventricle 610, and into the pulmonary artery 612. In the example of FIG. 6, the intracardiac blood pump assembly 602 includes one or more electrical sensors 606 located at or near a bend in the cannula 604. Here as well, electrical sensor 606 may be located on whatever portion of the bend (e.g., outside of the bend, inside of the bend, side of the bend) will position it optimally relative to the portion of the heart to be sensed. In the orientation shown in FIG. 6, the one or more electrical sensors 606 are positioned over the triangle of Koch such that the signals of the AV node 614 and/or the His bundle 616 can be sensed, and thus used for determining the location of the intracardiac blood pump assembly 602 relative to the patient's heart. Further electrical sensors may be included at other portions of the intracardiac blood pump assembly 602, such as at the distal end (not visible) or on an atraumatic extension at the distal end of the intracardiac blood pump assembly 602.

Figure 7:
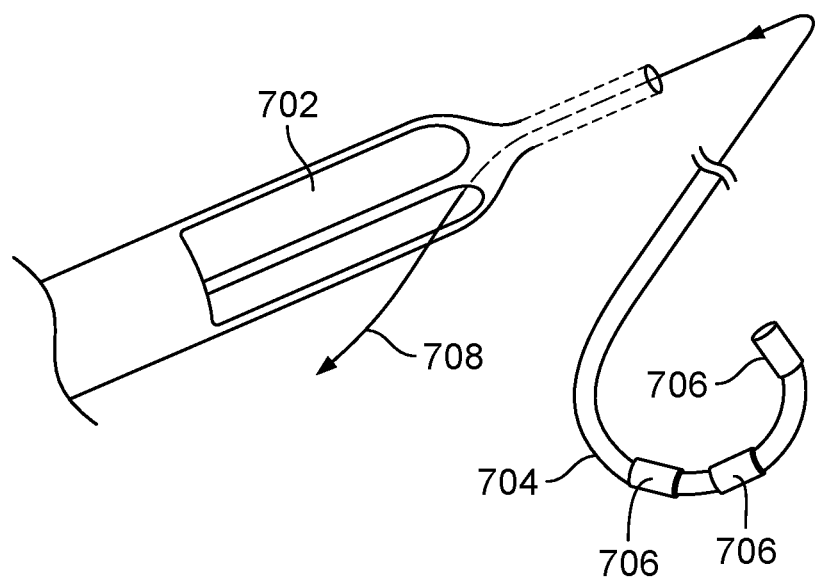
FIG. 7 is a sectional view of a distal end of an intracardiac blood pump assembly illustrating an exemplary sensor arrangement, in accordance with aspects of the disclosure.

FIG. 7 is a sectional view of a distal end of an intracardiac blood pump assembly illustrating one exemplary sensor arrangement, in accordance with aspects of the disclosure. This exemplary sensor arrangement may be used with any of the intracardiac blood pump assemblies described herein, including those of FIGS. 1, 2, 5, and 6. In that regard, FIG. 7 depicts an intracardiac blood pump assembly having a pigtail-shaped atraumatic extension 704 with three electrical sensors 706. As shown in FIG. 7, one or more wires 708 configured to carry the signal from the electrical sensors 706 extend down the inside of the atraumatic extension, into the distal end of cage 702 (e.g., a blood inflow or blood outflow cage), and out of one of the apertures of cage 702. Although the example of FIG. 7 shows three electrical sensors 706, the atraumatic extension 704 may include a single sensor, two sensors, or any other suitable number of sensors.

Figure 8A:
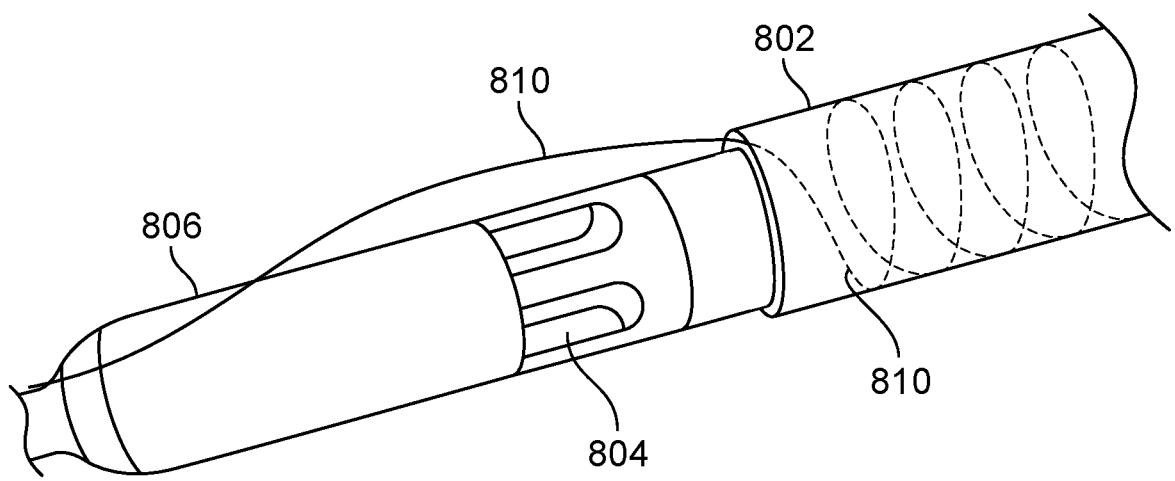
FIG. 8A is a sectional view of a portion of an intracardiac blood pump assembly illustrating one example of how wires from the sensor may exit the proximal end of the cannula in accordance with aspects of the disclosure.

FIG. 8A is a sectional view of a portion of an intracardiac blood pump assembly illustrating one example of how wires from the sensor may exit the proximal end of the cannula in accordance with aspects of the disclosure. In that regard, one or more wires 810 spiral around the cannula 802. The one or more wires 810 may spiral along an inner or outer surface of cannula 802, or may be embedded within the wall of cannula 802 (e.g., molded within the wall of cannula 802). The one or more wires 810 exit cannula 802 where the proximal end of cannula 802 meets up with cage 804 (e.g., a blood inflow or blood outflow cage). In that regard, the one or more wires 810 may exit cannula 802 by protruding out where cannula 802 overlaps with cage 804, or by passing through an aperture of cannula 802. The one or more wires 810 pass over motor 806 and continue in the proximal direction.

Figure 8B:
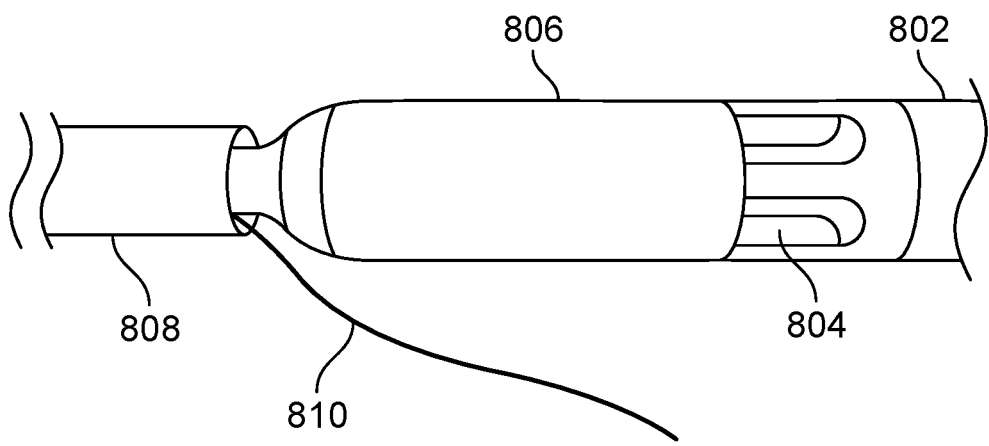
FIG. 8B is a sectional view of a portion of the intracardiac blood pump assembly of FIG. 8A illustrating one example of how wires from the sensor may enter the distal end of the catheter.

FIG. 8B is a sectional view of a portion of the blood pump assembly of FIG. 8A, illustrating one example of how the one or more wires 810 from the sensor may enter the distal end of the catheter 808. In that regard, all numerals shared between FIGS. 8A and 8B denote the same structures. As can be seen, in the example of FIG. 8B, the one or more wires 810 enter into catheter 808 where it overlaps with the proximal end of the housing of motor 806. In some aspects of the technology, the one or more wires 810 may run within a lumen of elongate catheter 808 out of the patient, where they will interface with a controller (e.g., controller 302 and device interface 312).

Figure 9:
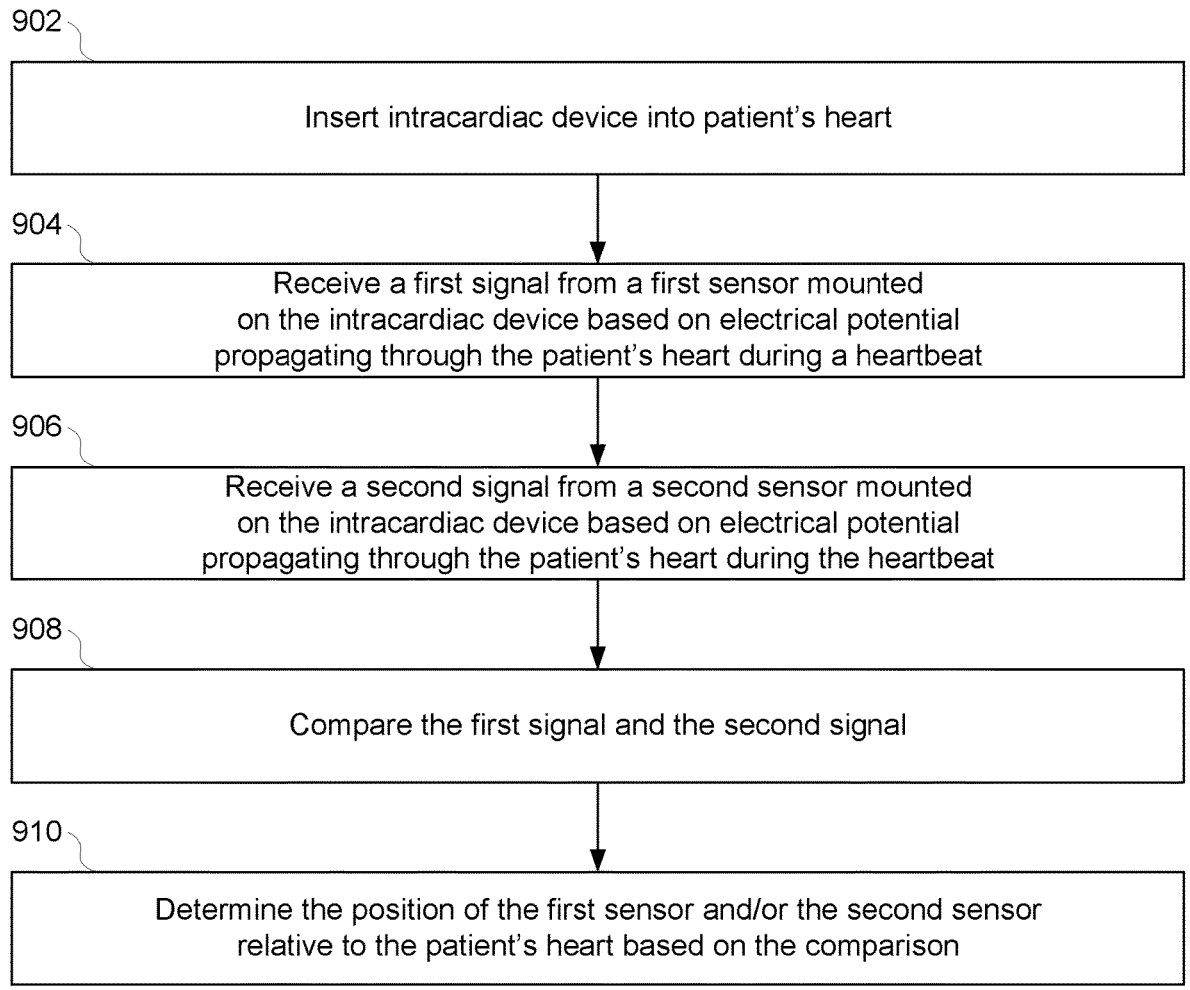
FIG. 9 is a flow diagram of an exemplary method for determining the position of an intracardiac device, in accordance with aspects of the disclosure.

FIG. 9 is a flow diagram of an exemplary method 900 for determining the position of an intracardiac device, in accordance with aspects of the disclosure. In that regard, in step 902, an intracardiac device is inserted into a patient's heart. This may involve any suitable intracardiac device, such as those described above with respect to FIGS. 1-8, and may be done in any suitable way, such as percutaneously via any of the catheterization procedures described above with respect to FIGS. 1 and 2.

In step 904, a first signal from a first sensor mounted on the intracardiac device is received, e.g., by a controller of the intracardiac device such as controller 302 of FIG. 3. In this example, the first sensor is an electrical sensor, and produces a first signal based on the electrical potential propagating through the patient's heart during a given heartbeat.

In step 906, a second signal from a second sensor mounted on the intracardiac device is received. Again, this second signal may be received by a controller of the intracardiac device, e.g., controller 302 of FIG. 3. In this example, the second sensor is also an electrical sensor, and produces a second signal which is also based on the electrical potential propagating through the patient's heart during the given heartbeat.

In step 908, the first signal received from the first sensor is compared to the second signal received from the second sensor. This may be done, for example, by one or more processors of the controller, e.g., processors 304 of controller 302 of FIG. 3.

In step 910, the position of the first sensor and/or the second sensor (and thus the intracardiac device) relative to the patient's heart is determined based on the comparison of the first signal and the second signal. This determination may be made based (in whole or in part) on the presence or absence of differences between any relevant criteria, such as the timing, shape, and/or amplitude of the respective first signal and second signal. Likewise, this determination may be further based on any other relevant criteria, such as a comparison of the first signal and/or the second signal to one or more reference signals (e.g., based on representative heart waves such as those shown in the illustrative diagram of FIG. 4), one or more prior signals received from the first sensor and/or the second sensor, a value based on one or more prior signals received from the first sensor and/or the second sensor (e.g., an average of those prior signals, or an average difference between a set of prior signals), or any combination thereof.

Figure 10:
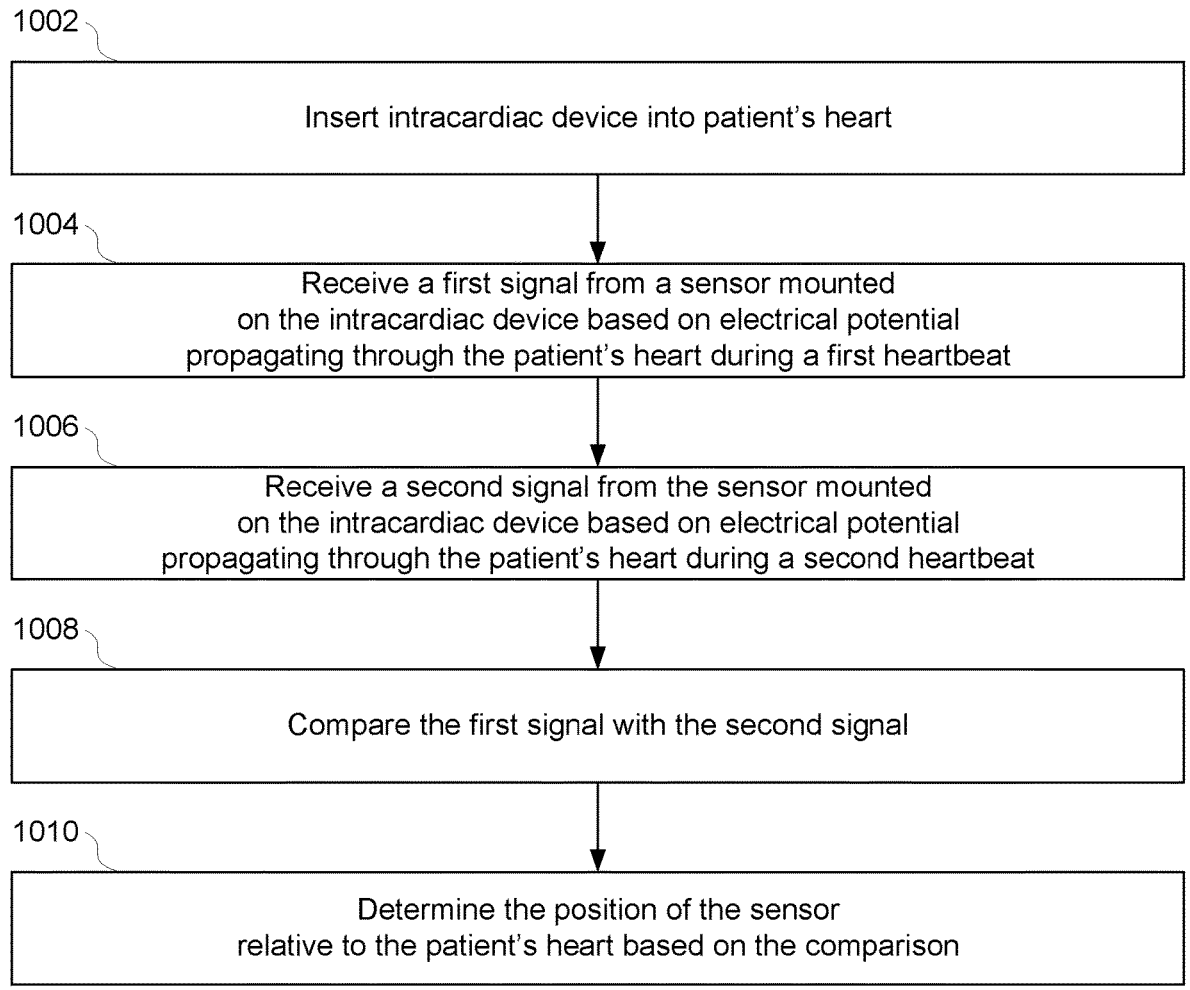
FIG. 10 is a flow diagram of an exemplary method for determining the position of an intracardiac device, in accordance with aspects of the disclosure.

FIG. 10 is a flow diagram of an exemplary method 1000 for determining the position of an intracardiac device, in accordance with aspects of the disclosure. In that regard, in step 1002, an intracardiac device is inserted into a patient's heart. Here again, this may involve any suitable intracardiac device, such as those described above with respect to FIGS. 1-8, and may be done in any suitable way, such as percutaneously via any of the catheterization procedures described above with respect to FIGS. 1 and 2.

In step 1004, a first signal from a sensor mounted on the intracardiac device is received, e.g., by a controller of the intracardiac device such as controller 302 of FIG. 3. In this example, the sensor is an electrical sensor, and produces a first signal based on the electrical potential propagating through the patient's heart during a first heartbeat.

In step 1006, a second signal from the sensor is received. This second signal may also be received by a controller of the intracardiac device, e.g., controller 302 of FIG. 3. In this example, the sensor is the same electrical sensor as in step 904, and produces a second signal which is based on the electrical potential propagating through the patient's heart during a second heartbeat. Although steps 1004 and 1006 use the terms "first" and "second," there may be one or more intervening heartbeats between the "first heartbeat" and the "second heartbeat," and there may be one or more intervening signals output by the sensor between the "first signal" and the "second signal."

In step 1008, the first signal received from the sensor is compared to the second signal received from the sensor. Here as well, this may be done, for example, by one or more processors of the controller, e.g., processors 304 of controller 302 of FIG. 3.

In step 1010, the position of the sensor (and thus the intracardiac device) relative to the patient's heart is determined based on the comparison of the first signal and the second signal. This determination may be made based (in whole or in part) on the presence or absence of differences between any relevant criteria, such as the timing, shape, and/or amplitude of the respective first signal and second signal. Likewise, this determination may be further based on any other relevant criteria, such as a comparison of the first signal and/or the second signal to one or more reference signals (e.g., based on representative heart waves such as those shown in the illustrative diagram of FIG. 4), one or more prior signals received from the sensor, a value based on one or more prior signals received from the sensor (e.g., an average of those prior signals, or an average difference between a set of prior signals), or any combination thereof.

From the foregoing and with reference to the various figures, those skilled in the art will appreciate that certain modifications can also be made to the present disclosure without departing from the scope of the same. While several aspects of the disclosure have been shown in the figures, it is not intended that the disclosure be limited thereto, as it is intended that the disclosure be as broad in scope as the art will allow and that the specification be read likewise. Therefore, the above description should not be construed as limiting, but merely as exemplifications of particular aspects of the present technology.

The invention claimed is:

1. A system for sensing position of an intracardiac device, comprising:
   an intracardiac device configured to be inserted into a patient's heart;
   two sensors mounted on the intracardiac device, placed in spaced apart locations and each configured to sense electrical pulses within the patient's heart; and
   one or more processors configured to receive one or more signals from each of the two sensors positioned on the intracardiac device, and, based at least in part on one or more signals received from each of the two sensors, the processor is configured to compare a shape of one or more signals received from a first sensor of the two sensors with a shape of one or more signals received from a second sensor of the two sensors to determine a location of a first of the two sensors relative to a location of a second of the two sensors, wherein smaller differences in signal shape indicate that the two sensors are closer together and differences that are larger indicate that the two sensors are further apart.

2. The system of claim 1, wherein the two sensors comprise a first sensor mounted at a first location on the intracardiac device, and a second sensor mounted at a second location on the intracardiac device.

3. The system of claim 1, wherein the one or more processors being configured to determine a relative location of the two sensors based at least in part on one or more signals received from the two sensors further comprises being configured to compare relative shapes to data regarding representative heart waves.

4. The system of claim 1, wherein the one or more processors being further configured to determine a relative location of the two sensors based at least in part on one or more signals received from the two sensors comprises being configured to compare relative timing of one or more signals received from a first sensor of the two sensors, and of one or more signals received from a second sensor of the two sensors.

5. The system of claim 4, wherein the one or more processors being further configured to determine a relative location of the two sensors based at least in part on one or more signals received from the two sensors further comprises being configured to compare the relative timing to data regarding representative heart waves.

6. The system of claim 1, wherein the one or more processors being further configured to determine a relative location of the two sensors based at least in part on one or more signals received from the two sensors comprises being configured to compare relative amplitudes of one or more signals received from the first sensor, and of one or more signals received from the second sensor.

7. The system of claim 6, wherein the one or more processors being further configured to determine a relative location of the two sensors based at least in part on one or more signals received from the two sensors further comprises being configured to compare the relative amplitudes to data regarding representative heart waves.

8. The system of claim 1, wherein the one or more processors being configured to determine a relative location of the two sensor based at least in part on one or more signals received from the two sensors comprises being configured to compare one or more signals received from the two sensors during a first heartbeat to one or more signals received from the two sensors during a second heartbeat.

9. The system of claim 8, wherein the one or more processors are further configured to determine a position of the intracardiac device based at least in part on a predetermined position of the intracardiac device within the patient's heart.

10. The system of claim 9, wherein the one or more processors being configured to determine a position of the intracardiac device based at least in part on one or more signals received from the two sensors comprises being configured to determine whether a difference between the one or more signals received from the two sensors during the first heartbeat and the one or more signals received from the two sensors during the second heartbeat indicates that the intracardiac device has moved from the predetermined position.

11. The system of claim 1, wherein the intracardiac device comprises an intracardiac blood pump.

* * * * *